United States Patent

Brechbuhler et al.

[11] 3,993,662
[45] Nov. 23, 1976

[54] INSECTICIDAL N-(SUBSTITUTED PHENYL)-TRICYCLO [3,2,2,0$^{2,4}$]NONANE-6,7-DICARBOXIMIDES

[75] Inventors: Hans U. Brechbühler, Basel; Jean Claude Petitpierre, Kaiseraugst, both of Switzerland

[73] Assignee: Ciba-Geigy Corporation, Ardsley, N.Y.

[22] Filed: Oct. 28, 1975

[21] Appl. No.: 626,395

Related U.S. Application Data

[63] Continuation of Ser. No. 459,434, April 9, 1974, abandoned.

[52] U.S. Cl............................ 260/326 C; 424/274
[51] Int. Cl.$^2$........................................ C07D 209/48
[58] Field of Search ............................ 260/326 C

[56] References Cited
UNITED STATES PATENTS
2,545,283    3/1951    Johnson ............................ 260/326 C
FOREIGN PATENTS OR APPLICATIONS
1,056,908   2/1967    United Kingdom ............. 260/326 C

*Primary Examiner*—Elbert L. Roberts
*Assistant Examiner*—S. P. Williams
*Attorney, Agent, or Firm*—Harry Falber

[57] ABSTRACT

New dicarboximides of the formula

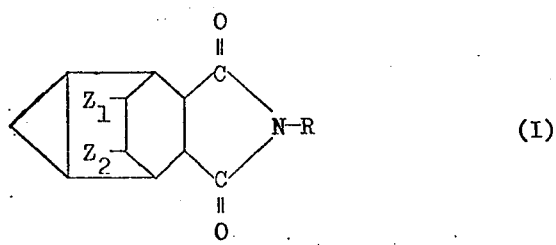

(I)

wherein
R represents a phenyl mono- to trisubstituted, identically or differently, by fluorine, chlorine, bromine, iodine, trifluoromethyl, nitro, cyano, $C_1$—$C_4$-alkyl, methoxy or methylthio, or monosubstituted by a methylenedioxy group, and
$Z_1$ and $Z_2$ each represent hydrogen, or together with the carbon atoms to which they are bound they represent a carbon-carbon bond
and their use for controling insects are disclosed.

9 Claims, No Drawings

INSECTICIDAL N-(SUBSTITUTED PHENYL)-TRICYCLO [3,2,3,0$^{2,4}$]NONANE-6,7-DICARBOXIMIDES

This is a continuation of application Ser. No. 459,434 filed on Apr. 9, 1974, and now abandoned.

The present invention relates to dicarboximides, to processes for their preparation, and to their use for the control of insects.

The dicarboximides correspond to the formula

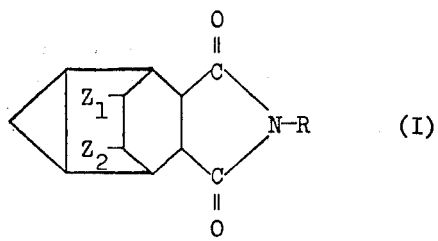

wherein

R represents a phenyl mono- to trisubstituted, identically or differently, by fluorine, chlorine, bromine, iodine, trifluoromethyl, nitro, cyano, $C_1$–$C_4$-alkyl, methoxy or methylthio, or monosubstituted by a methylenedioxy group, and $Z_1$ and $Z_2$ each represent hydrogen, or together with the carbon atoms to which they are bound they represent a carbon-carbon bond.

As substituents of the phenyl group, the $C_1$–$C_4$-alkyl groups can be branched-chain or straight-chain, and are preferably the methyl or ethyl group.

Compounds of formula I preferred by virtue of their action are those wherein

R represents a phenyl mono- to trisubstituted, identically or differently, by fluorine, chlorine, bromine, iodine, trifluoromethyl, methyl, ethyl, methoxy, methylthio, nitro or cyano, or monosubstituted by a methylenedioxy group, and $Z_1$ and $Z_2$ each represent hydrogen, or together with the carbon atoms to which they are bound they represent a carbon-carbon bond.

Particularly preferred compounds of formula I are those wherein

R represent a phenyl mono- to trisubstituted, identically or differently, by fluorine, chlorine, bromine, iodine, trifluoromethyl, ethyl, methylthio, nitro or cyano, or monosubstituted by a methylenedioxy group, and $Z_1$ and $Z_2$ together with the carbon atoms to which they are bound represent a carbon-carbon bond.

The compounds of formula I can be prepared by methods known per se; for example, by reaction of a compound of the formula

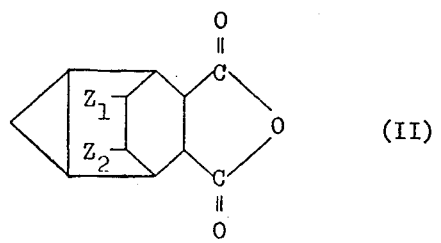

with a compound of the formula $$H_2N-R$$

wherein R, $Z_1$ and $Z_2$ have the meanings given for formula I.

The reaction is performed under normal pressure, at a temperature of 60° – 150° C, preferably 80° – 120° C, and in a high-boiling solvent, such as, e.g. glacial acetic acid, benzene, toluene or xylene.

The starting materials of formula II are known, and can be prepared by a method analogous to that described in Ber. 86, 1528–39 (1953).

The compounds of formula I are suitable for the control of insects. To be particularly emphasised is their high degree of effectiveness against Lepidoptera.

In the U.S. Pat. Nos. 2,462,835 and 2,545,283, dicarboximides are described as synergists. Reference is made to, inter alia, their insecticidal action.

The insecticidal, herbicidal and fungicidal action of dicarboximides is described in the U.S. Pat. No. 3,654,302.

Compared with the compounds described in the abovementioned patent specifications, the dicarboximides of formula I exhibit an unexpectedly better larvicidal action, especially in the case of larvae of Lepidoptera.

The insecticidal action of the dicarboximides of formula I can be appreciably broadened and adapted to suit given circumstances by the addition of other insecticides. Suitable additives are, for example:

organic phosphorous compounds,
nitrophenols and derivatives thereof,
formamidines,
carbamates and
chlorinated hydrocarbons.

The compounds of formula I can be used on their own or together with suitable carriers and/or additives. Suitable carriers and additives may be solid or liquid, and they correspond to the substances common in formulation practice, such as, e.g. natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

Solid Preparations: dusts, scattering agents, granulates, coated granulates, impregnated granulates and homogeneous granulates;

Liquid Preparations
a. water-dispersible active-substance concentrates: wettable powders, pastes or emulsions;
b. solutions.

The content of active substance in the described agents is between 0.1 and 95 %.

The active substances of formula I can be formulated, for example, as follows:

Dusts

The following substances are used in the preparation of (a) a 5% dust, and (b) a 2% dust:

| a) | 5 parts of active substance, |
| | 95 parts of talcum; |
| b) | 2 parts of active substance, |
| | 1 part of highly dispersed silicic acid, |
| | 97 parts of talcum. |

The active substances are mixed and ground with the carriers.

Granulate

The following substances are used to prepare a 5% granulate:

| 5 | parts of active substance, |
| 0.25 | parts of epichlorohydrin, |
| 0.25 | part of cetyl polyglycol ether, |
| 3.50 | parts of polyethylene glycol, |
| 91 | parts of kaolin (particle size 0.3 – 0.8 mm) |

The active substance is mixed with epichlorohydrin and dissolved with 6 parts of acetone; the polyethylene glycol and cetyl polyglycol ether are then added. The solution thus obtained is sprayed onto kaolin, and the acetone subsequently evaporated off in vacuo.

Wettable powder

The following constituents are used for the preparation of (a) a 40%, (b) and (c) a 25%, and (d) a 10% wettable powder:

| a) | 40 | parts of active substance, |
| | 5 | parts of sodium lignin sulphonate, |
| | 1 | part of sodium dibutyl-naphthalene sulphonate, |
| | 54 | parts of silicic acid; |
| b) | 25 | parts of active substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silicic acid, |
| | 19.5 | parts of Champagne chalk, |
| | 28.1 | parts of kaolin; |
| c) | 25 | parts of active substance, |
| | 2.5 | parts of isooctylphenoxy-polyoxyethylene-ethanol, |
| | 1.7 | parts of Champagne chalk/hydroxyethyl cellulose mixture (1:1), |
| | 8.3 | parts of sodium aluminium silicate, |
| | 16.5 | parts of kieselguhr, |
| | 46 | parts of kaolin; |
| d) | 10 | parts of active substance, |
| | 3 | parts of a mixture of the sodium salts of saturated fatty alcohol sulphates, |
| | 5 | parts of naphthalenesulphonic acid/formaldehyde condensate, |
| | 82 | parts of kaolin. |

The active substances are intimately mixed, in suitable mixers, with the additives, the mixture being then ground in the appropriate mills and rollers. Wettable powders are obtained which can be diluted with water to give suspensions of any desired concentration.

Emulsifiable Concentrates

The following substances are used to prepare (a) a 10% and (b) a 25% emulsifiable concentrate:

| a) | 10 | parts of active substance, |
| | 3.4 | parts of epoxidised vegetable oil, |
| | 3.4 | parts of a combination emulsifier consisting of fatty alcohol polyglycol ether and alkylarylsulphonate calcium salt, |
| | 40 | parts of dimethylformamide, |
| | 43.2 | parts of xylene; |
| b) | 25 | parts of active substance, |
| | 2.5 | parts of epoxidised vegetable oil, |
| | 10 | parts of an alkylarylsulphonate/fatty alcohol polyglycol ether mixture, |
| | 5 | parts of dimethylformamide, |
| | 57.5 | parts of xylene. |

From these concentrates it is possible to prepare, by dilution with water, emulsions of any desired concentration.

Spray

The following constituents are used to prepare a 5% spray:

| 5 | parts of active substance, |
| 1 | part of epichlorhydrin, |
| 94 | parts of ligroin (boiling limits 160 – 190° C). |

EXAMPLE 1 a. Preparation of
N-(4'-nitrophenyl)-tricyclo-[3.2.2.0$^{2.4}$]-non-8-ene-6,7-dicarboximide 250 g of tricyclo-[3.2.2.0$^{2.4}$]-non-8-ene-6,7-dicarboxylic acid anhydride (prepared from cycloheptatriene and maleic acid anhydride, K. Alder, Ber. 86, 1528–39 (1953)) and 200 g of 4-nitroaniline are refluxed in 1500 ml of glacial acetic acid for 3 hours. The reaction mixture cooled to 60° C is poured into 2000 ml of hot water, whereupon the crude product precipitates. After cooling, the crude product is filtered off, dried, and recrystallised from ethyl acetate; M.P. 210°–212° C.

b. Preparation of
N-(3',5'-dichlorophenyl)-tricyclo-[3.2.2.0$^{2.4}$]-nonane-6,7-dicarboximide 19.2 g of tricyclo-[3.2.2.0$^{2.4}$]-nonane-6,7-dicarboxylic acid anhydride (prepared from the cycloheptatriene/maleic acid anhydride adduct (see Ex. 1a) by catalytic hydrogenation, K. Alder, Ber. 86, 1528–39 (1953) and 19.4 g of 3,5-dichloroaniline are refluxed in 1000 ml of toluene for 16 hours, whereby the water forming during the reaction is separated with a water separator. After cooling, the toluene is removed in vacuum, and the residue recrystallised from ethyl acetate, M.P. 145° – 153° C.

The following additional compounds are prepared in an analogous manner:

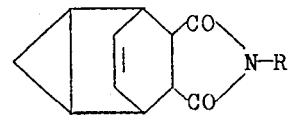

| R= | M.P. ° C |
|---|---|
| 3,4-dichlorophenyl | 204 – 206° C |
| 4-bromophenyl | 206 – 207° C |
| 4-fluorophenyl | 184° C |
| 4-chlorophenyl | 203° C |
| 3-trifluoromethyl-phenyl | 206° C |
| 3-methylthio-phenyl | 186 – 188° C |
| 3,5-dichlorophenyl | 167 – 169° C |
| 2,4,5-trichlorophenyl | 168 – 170° C |
| 2,5-dibromophenyl | 191 – 192° C |
| 2,5-dichlorophenyl | 195 – 196° C |
| 3-chlorophenyl | 182 – 183° C |
| 3-nitrophenyl | 204 – 206° C |
| 3,5-bis-trifluoromethyl-phenyl | 100 – 101° C |
| 2-chloro-5-trifluoromethyl-phenyl | 126 – 127° C |
| 2-ethyl-phenyl | 152 – 154° C |
| 4-cyano-phenyl | 190 – 191° C |
| 2-methyl-4-chlorophenyl | 179 – 180° C |
| 2-methyl-5-chlorophenyl | 184 – 190° C |
| 3-trifluoromethyl-4-chlorophenyl | 189 – 190° C |
| 2-methyl-5-nitrophenyl | 189 – 190° C |
| 2-nitrophenyl | 168 – 170° C |
| 4-methoxy-phenyl | 198 – 200° C |
| 2-fluorophenyl | 148 – 149° C |
| 3-fluorophenyl | 152 – 154° C |
| 2-iodophenyl | 149 – 151° C |
| 4-iodophenyl | 216 – 218° C |
| 2-chloro-4-bromophenyl | 208 – 210° C |
| 2,5-dimethoxy-4-chlorophenyl | 196 – 198° C |
| 4-methylthio-phenyl | 186 – 188° C |
| 3,5-dinitro-phenyl | 178 – 180° C |
| 2-nitro-4-methyl-phenyl | 202 – 204° C |
| 2,4-dichlorophenyl | 162 – 164° C |
| 2-trifluoromethyl-phenyl | 128° C |
| 2-methyl-3-chlorophenyl | 157° C |
| 3,4-methylenedioxy-phenyl | 217° C |
| 4-trifluoromethylphenyl | 218° C |
| 2-methoxy-4-chlorophenyl | 170° C |
| 2,4-dibromophenyl | 207° C |
| 2,4-difluorophenyl | 135° C |
| 2,5-difluorophenyl | 135° C |
| 2-methyl-4-bromophenyl | 198° C |
| 3-fluoro-4-methyl-phenyl | 202° C |
| 3-bromo-5-trifluoromethyl-phenyl | 141° C |
| 3,4,5-trichlorophenyl | 186 – 187° C |
| 2-methyl-3-nitrophenyl | 210° C |
| 4-bromophenyl | 230 – 240° C |
| 2-chloro-5-trifluoromethyl-phenyl | 157° C |
| 2,4-dichlorophenyl | 175° C |

EXAMPLE 2

Insecticidal action against *Spodoptera littoralis*

Cotton plants 15 cm in height were sprayed with 25 ml of a solution (acetone/water 1:1) containing 0.2% of active substance. After drying of the coating, 5 SPODOPTERA LITTORALIS caterpillars (L₃ stage) were placed on each plant. A plastic cylinder was put over the plant and closed with a copper gauze lid. A mortality determination was made after 2 days. The compounds according to Example 1 exhibited in this test a good action against *Spodoptera littoralis*.

EXAMPLE 3

Insecticidal action against *Leptinotarsa decemlineata*

Potato plants 15 cm in height were sprayed with 25 ml of a solution (acetone/water 1:1) containing 0.1% of active substance. After drying of the coating, 10 Leptinotarsa larvae (L₃ stage) were placed on each plant. A plastic cylinder was put over the plant and closed with a copper gauze lid. A mortality evaluation was made after 2 days.

The compounds according to Example 1 exhibited in this test a good action *Leptinotarsa decemlineata*.

We claim:

1. A compound of the formula

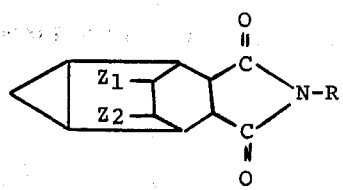

wherein R represents a phenyl mono- to trisubstituted, identically or differently, by fluorine, chlorine, bromine, iodine, trifluoromethyl, ethyl, methylthio, nitro or cyano, or monosubstituted by a methylendioxy group, and $Z_1$ and $Z_2$ together with the carbon atoms to which they are bound represent a carbon-carbon bond.

2. Compound according to claim 1 of the formula

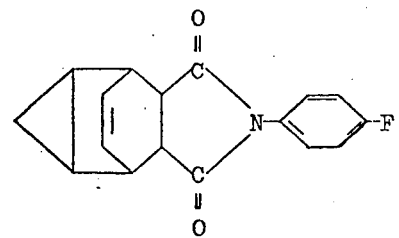

3. Compound according to claim 1 of the formula

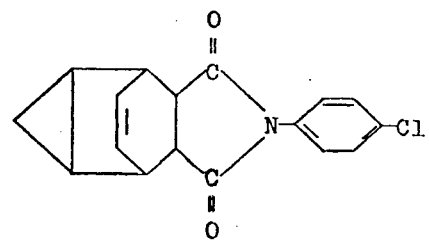

4. Compound according to claim 1 of the formula

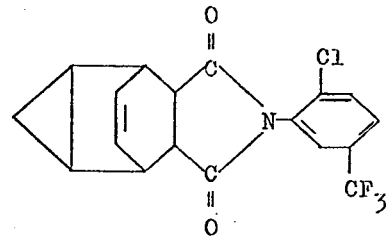

5. Compound according to claim 1 of the formula

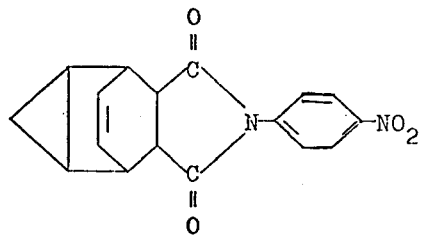

6. Compound according to claim 1 of the formula
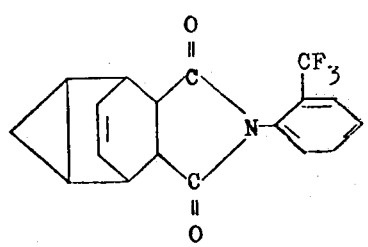
7. Compound according to claim 1 of the formula
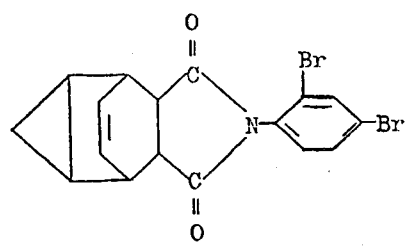
8. Compound according to claim 1 of the formula
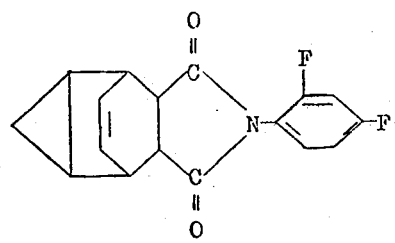
9. Compound according to claim 1 of the formula
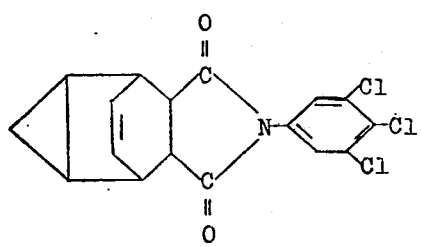
* * * * *